United States Patent [19]

D'Silva

[11] Patent Number: 4,485,113

[45] Date of Patent: * Nov. 27, 1984

[54] CARBAMIC PESTICIDAL COMPOSITIONS

[75] Inventor: Themistocles D. J. D'Silva, South Charleston, W. Va.

[73] Assignee: Union Carbide Corporation, Danbury, Conn.

[ * ] Notice: The portion of the term of this patent subsequent to Mar. 21, 1995 has been disclaimed.

[21] Appl. No.: 11,645

[22] Filed: Feb. 12, 1979

Related U.S. Application Data

[63] Continuation of Ser. No. 701,165, Jun. 30, 1976, abandoned.

[51] Int. Cl.[3] ........ A01N 47/10

[52] U.S. Cl. ........ 424/304; 424/298; 424/300; 560/115; 560/121; 560/165

[58] Field of Search ........ 260/306.71, 453 R; 424/304, 298, 300

[56] References Cited

U.S. PATENT DOCUMENTS

| | | | |
|---|---|---|---|
| 3,825,579 | 7/1974 | Fujimoto et al. | 260/453 R |
| 3,890,386 | 6/1975 | Kuhle et al. | 260/566 |
| 3,939,192 | 2/1976 | Kühle et al. | 260/453 R |
| 4,008,328 | 2/1977 | Siegle et al. | 424/298 |
| 4,029,688 | 6/1977 | D'Silva | 260/465.4 |
| 4,080,469 | 3/1978 | D'Silva | 424/298 |
| 4,169,894 | 10/1979 | D'Silva | 424/277 |
| 4,315,928 | 2/1982 | Thurman | 424/304 |

*Primary Examiner*—Nicholas S. Rizzo
*Attorney, Agent, or Firm*—John A. Shedden

[57] ABSTRACT

N-(Substituted alkanesulfenyl)-N-alkyl and N-(substituted alkanethiosulfenyl)-N-alkyl carbamate compounds exhibit pesticidal activity against a broad range of pests.

24 Claims, No Drawings

CARBAMIC PESTICIDAL COMPOSITIONS

This application is a continuation of our prior U.S. application: Ser. No. 701,165 Filing Date June 30, 1976 now abandoned.

This invention relates to novel N-(Substituted alkanethiosulfenyl)-N-alkyl and N-(substituted alkanesulfenyl)-N-alkyl carbamates and to their preparation. This invention is also directed to insecticidal, miticidal and nematocidal compositions comprising an acceptable carrier and an insecticidally, miticidally or nematocidally effective amount of a compound according to this invention as well as to a method of controlling insects, mites and nematodes by subjecting them to an insecticidally, nematocidally or miticidally effective amount of a compound of this invention.

More particularly, this invention relates to compounds of the formula:

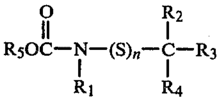

wherein:

n is 1 or 2;

$R_1$ is alkyl;

$R_2$ and $R_3$ are individually alkyl, haloalkyl or $R_2$ and $R_3$ together may form an alkylene chain completing either a substituted or an unsubstituted cyclopentyl, cyclohexyl or a 6, 7 or 8 membered bicycloalkyl ring wherein the permissible substituents are one or more chloro, fluoro, bromo, alkyl or haloalkyl substituents in any combination;

$R_4$ is hydrogen, alkyl, chloro or cyano;

$R_5$ is

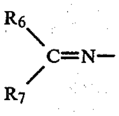 or 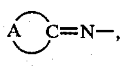, wherein:

$R_6$ is hydrogen, chloro, cyano, alkyl, alkylthio or cyanoalkylthio;

$R_7$ is chloro, carbamoyl, alkylcarbamoyl, amido, dialkylcarbamoyl, dithiolanylalkyl or either substituted or unsubstituted alkyl, alkenyl, alkylthio, alkoxyalkyl, alkanoyl, phenyl or alkoxycarbonyl wherein the permissible substituents are one or more fluoro, chloro, bromo, cyano, nitro, alkylthio, alkylsulfinyl, alkylsulfonyl, alkoxy, carbamoyl, alkylcarbamoyl or dialkylcarbamoyl substituents; and A is a divalent alkylene chain having from 2 to 24 aliphatic carbon atoms completing a five or six membered alicyclic ring which includes one, two or three groups selected from among oxygen, sulfur, sulfinyl, sulfonyl,

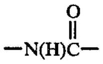 or 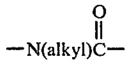

in any combination, provided that;

(I) said groups are separated by at least one carbon atom;

(II) not more than one of said groups may be

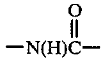 or 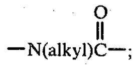;

and (III) not more than two of said groups may be oxygen.

The carbamate compounds of this invention exhibit outstanding miticidal and insecticidal activity. Certain of these compounds also exhibit excellent nematocidal activity. They are relatively non-toxic to plants and mammals when used in amounts sufficient to kill mites, insects and nematodes.

In general, $R_1$, $R_2$, $R_3$, $R_4$, $R_6$, $R_7$, $R_8$ and $R_9$ substituents individually may not include more than 8 aliphatic carbons. Preferred because of their higher level of pesticidal activity are the compounds of this invention wherein:

$R_1$ is alkyl having from 1 to 4 carbons;

$R_2$ and $R_3$ are individually alkyl or chloroalkyl;

$R_5$ is

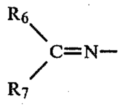 or 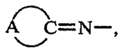, wherein:

$R_6$ is hydrogen, alkyl, alkylthio or cyanoalkylthio;

$R_7$ is alkyl, alkylthio, alkoxycarbonyl, carbamoyl, alkylcarbamoyl, dialkylcarbamoyl, alkylthioalkyl, alkylsulfinylalkyl, alkylsulfonylalkyl, cyanoalkyl, nitroalkyl or cyanoalkylthio;

A is a divalent alkylene chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 3-oximinothiophane, 2-oximinothiophane, 2-oximino-tetrahydro-1,4-oxazin-3-one, 2-oximino-1,3,5-trithiane, 4-oximino-1,3,5-oxadithiane, 2-oximino-1,4-oxathiane, 4-oximino-1,3-oxathiolane, 2-oximinothiazolidin-3-one, 2-oximino-1,3-thiazolidin-4-one or 2-oximino-tetrahydro-1,4-thiazin-5-one ring, wherein sulfur may be in any of its oxidation states or in any combination thereof. Particularly preferred compounds of this invention are those in which $R_1$ is methyl, $R_2$ and $R_3$ are individually methyl or chloromethyl or $R_4$ is cyano or chloromethyl.

The compounds of this invention can be prepared by reacting the corresponding carbamoyl halide with an appropriately substituted oxime in the presence of a suitable acid acceptor as illustrated in the following reaction scheme:

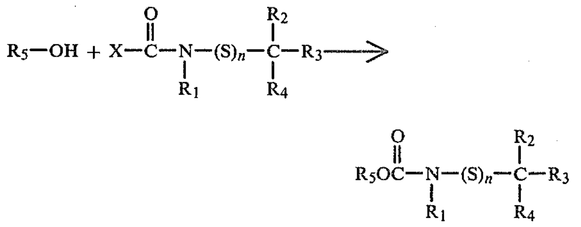

n, $R_1$, $R_2$, $R_3$, $R_4$ and $R_5$ are described above and X is either fluorine or chlorine.

The reaction can be carried out by bringing together substantially equimolar amounts of the reactants in an inert solvent. In general any inert solvent can be employed in the conduct of this reaction. Illustrative of inert solvents that are useful in the conduct of this reaction are benzene, toluene, xylene, dioxane, tetrahydrofuran, ethylether, cyclohexane, methylene chloride and the like.

The reaction is conducted in the presence of an acid acceptor. The quantity of acid acceptor employed is usually substantially equivalent to the quantity of either the oxime or the carbamoyl halide reactant. The acid acceptor is a basic material which can be either an organic or inorganic base. Inorganic bases, such as sodium hydroxide, potassium hydroxide or the like and organic bases, such as tertiary amines, alkali metal alkoxides or the like are illustrative of bases which are useful as acid acceptors. Preferred acid acceptors are tertiary amines, such as triethylamine, pyridine, 1,4-diazabicyclo [2.2.2] octane or the like.

The reaction can be conducted in either a homogeneous phase system or a heterogeneous phase system. In the latter case, a phase transfer, such as a crown ether or a quaternary ammonium halide compound, can be used to facilitate the transfer of the reactants across the phase interface.

Reaction temperatures are not critical and may be varied over a wide range depending to a large extent on the reactivity and the thermal stability of the reactants. In most cases the reaction goes to completion at room temperature. If either reduced or extended reaction times are desired, the reaction can be conducted at a temperature of from about −50° C. to about 100° C. The preferred reaction temperature range is from about 0° C. to about 40° C.

Reaction pressures are not critical. For convenience, the reaction is usually conducted at atmospheric or autogeneous pressure.

Oxime precursors of the formula:

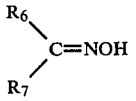

in which $R_6$ and $R_7$ are as described above, can be conveniently prepared according to a variety of methods. For example, 2-methylthio-2-methylpropionaldoxime can be prepared by chlorinating 2-methylpropanal to form 2-chloro-2-methylpropanal which is then treated with sodium methylmerceptide to form 2-methylthio-2-methylpropanal which, in turn, is treated with hydroxylamine hydrochloride to form the desired oxime precursor. The above disclosed method together with other methods useful for preparing oxime precursors are described in more detail in the U.S. Pat. No. 3,843,669, 3,217,036, 3,217,037, 3,400,153, 3,536,760, and 3,576,834.

Alicyclic oxime precursors, of the formula:

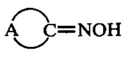

used in the preparation of the carbamate compounds of this invention can be prepared by a variety of methods, the choice of method being influenced to a large extent by the types and number of hetero groups included within the alicyclic ring. For example:

A. 2-oximino-1,3,5-trithiane, 4-oximino-1,3-oxazolidin-4-one, 4-oximino-1,3,5-oxadithiane and 2-oximino-1,4-oxazine-3-one compounds can be conveniently prepared by sequentially treating the corresponding 1,3,5-trithiane, 1,3-oxazolidin-4-one, 1,3,5-oxadithiane or 1,4-oxazin-3-one compound with a base and an alkyl nitrite ester followed by neutralization with a suitable organic or inorganic acid. For example, 2-oximino-4-methyltetrahydro-1,4-oxazin-3-one can be prepared by treating 4-methyltetrahydro-1,4-oxazin-3-one with potassium t-butoxide followed by the addition of isobutyl nitrite. The reaction is conducted in anhydrous tetrahydrofuran. After the reaction has gone to completion in about 3 hours the resulting oxime salt is neutralized with hydrochloric acid.

B. 2-oximino-tetrahydro-1,4-thiazine-3-one compounds can be prepared by reacting ethoxycarbonylformhydroxamoyl chloride with the sodium salt of an appropriately substituted alkylaminoalkane mercaptan in an aprotic solvent, such as benzene, chloroform and the like. This reaction is described in more detail in U.S. Pat. No. 3,790,560.

C. 3-oximino-1,4-oxathiane or 4-oximino-1,3-oxathiolane compounds can be prepared according to the method disclosed in Belgium Patent No. 813,206 and United States patent application Ser. No. 347,446 filed Apr. 3, 1973.

D. 4-oximino-1,3-dithiolane and 2-oximino-1,4-dithiane compounds can be prepared by reacting equivalent amounts of 2-haloalkanehydroxamoyl halide with the sodium salt of an appropriately substituted alkanedithiol in an aprotic solvent like benzene, methylene chloride or ethanol. For example 2-oximino-3,3-dimethyl-1,4-dithiane can be prepared by adding 1,2-ethanedithiol to sodium ethoxide, thereby producing the sodium salt of 1,2-ethanedithiol in situ and then achieving cyclization by the addition of 2-chloro-2-methylpropionhydroxamoyl chloride.

Carbamoyl halide precursors employed in the preparation of the compounds of this invention can be prepared according to a variety of methods, the choice of method being influenced to a large extent by X and the value of n. For example;

(I) N-Thiosulfenyl carbamoyl chloride precursors can be prepared by reacting the corresponding sulfenyl chloride with an appropriately substituted mercaptan.

(II) N-Thiosulfenyl and N-sulfenyl carbamoyl fluoride precursors can be prepared by reacting hydrogen fluoride with an appropriately substituted isocyanate, thereby producing the corresponding N-alkyl carbamoyl fluoride in situ which is then reacted with either a thiosulfenyl chloride or a sulfenyl chloride compound to form the corresponding N-thiosulfenyl or N-sulfenyl carbamoyl fluoride compound, respectively. The above disclosed reactions together with other reactions which may be used to prepare the carbamoyl halide precursors are described in more detail in my United States patent application Ser. No. 706,166 filed 6/30/76 now U.S. Pat. No. 4,058,549 entitled N-(Substituted-alkanesulfenyl-N-Alkyl and N-(Substituted alkanethiosulfenyl)-N-Alkyl Carbamoyl Halide Compounds filed concurrently herewith.

The following specific examples are presented to particularly illustrate the invention.

EXAMPLE I

Preparation of N-Methyl-N-(2-chloromethyl-2-propanesulfenyl)carbamoyl Chloride

To a solution of 22.1 g of isobutylene in 150 ml of benzene was added dropwise and with external cooling (5°-10° C.), 48.0 g of N-methyl-N-chlorosulfenyl carbamoyl chloride dissolved in 150 ml of benzene. The reaction mixture was then stirred for an additional 1 hour at ambient temperature. Evaporation of the solvent gave 62.7 g of a (1:1) isometric mixture of product. The Markownikoff addition product decomposes on heating to yield isobutylene sulfide and other unidentified byproducts. The desired N-methyl-N-(2-chloromethyl-2-propanesulfenyl) carbamoyl chloride was isolated by distillation. b.p. 87°-90° C./0.4 mm.

Infra-red (neat) 5.82 (C═O), 8.0, 8.65, 9.8, 11.8, 12.5, 13.3 and 14.0μ.

NMR($CDCl_3$) δ1.40 (s), 6H; 3.49 (s), 3H; 3.78 (s), 2H.

EXAMPLE II

Preparation of N-Methyl-N-(2-methyl-1,3-dichloro-2-propanesulfenyl)carbamoyl chloride To a solution of 16.0 g of N-methyl-N-chlorosulfenyl carbamoyl chloride in 100 ml of methylene chloride was added 12.0 g of methallyl chloride with stirring, at room temperature. On slight heating there was a spontaneous exotherm which raised the temperature of the reaction mixture to 39° C. On removal of the solvent under reduced pressure 19.6 g of oil was obtained, $N^{25}D$ 1.5379.

Infra-red (neat), 5.76(C═O), 8.0, 8.65, 9.8, 11.8, 12.25, 13.45 and 14.0μ.

NMR($CDCl_3$) δ1.41 (s), 3H; 3.48 (s), 3H; 3.87 (d). $J_{AB}$=12.0 $H_Z$ and 3.97 (d), $J_{BA}$=12.0 $H_Z$ 4H.

Calc'd. for $C_6H_{10}Cl_3NOS$: C, 28.76; H, 4.02; N, 5.59. Found: C, 28.87; H, 3.87; N, 4.72.

EXAMPLE III

Preparation of N-Methyl-N-(1-chloro-2-cyano-2-propanesulfenyl)carbamoyl fluoride To a mixture of 3.53 g of anhydrous hydrogen fluoride in 150 ml of toluene cooled to −50° C. was added dropwise 10.05 g of methyl isocyanate. After stirring for 1.5 hr. at 0° C., 30.0 g of approximately 85 percent pure 1-chloro-2-cyano-2-propanesulfenyl chloride was added followed by dropwise addition of 17.8 g of triethylamine. During the addition of base the temperature was maintained between 0° and 10° C. After stirring for an additional 1 hr., the precipitated salt was removed by filtration and the filtrate was concentrated to yield 26.5 g of a light yellow oil.

Infra-red (neat) 4.53 (C≡N), 5.6 (C═O), 6.4, 6.9, 7.05, 7.3, 7.7, 8.5, 9.2, 9.4, 10.4, 12.4, 13.3μ.

NMR ($CDCl_3$) δ1.65 (s), 3H: 3.50 (s), 3H; 3.73 (d), $J_{AB}$=12.0 $H_Z$ and 3.98 (d), $J_{BA}$=12.0 $H_Z$, 2H.

EXAMPLE IV

Preparation of N-Methyl-N-(2-methyl-1,3-dichloro-2-propanesulfenyl)carbamoyl fluoride To a solution of 1.35 g of methallyl chloride in 25 ml of methylene chloride was added 2.15 g of N-methyl-N-chlorosulfenyl carbamoyl fluoride. The solution was heated to reflux for 45 min. and concentrated to 1.68 g of pale yellow oil.

Infra-red (neat) 5.57 (C═O), 6.9, 7.0, 7.26, 7.65, 8.45, 9.15, 10.42, 12.3, 13.3 and 14.1μ.

NMR ($CDCl_3$) δ1.39 (s), 3H; 3.36 (d), J=1.0 $H_Z$, 3H, 3.92 (s), 4H.

EXAMPLE V

Preparation of N-Methyl-N-(2-cyano-2-propanesulfenyl) carbamoyl Chloride

Anhydrous hydrochloric acid gas was bubbled for 20 min. through a mixture of 16.0 g of N-methyl-N-chlorosulfenyl carbamoyl chloride and 7.59 g of isobutyronitrile. After stirring for 26 hrs. the reaction mixture was distilled to yield 12.4 g of yellow oil. b.p. 50° C./8 mm. $N_D^{24}$ 1.4656.

Infra-red (neat) 4.43 (C≡N), 5.72 (C═O), 6.5, 6.85, 8.1, 8.6, 9.75 and 11.8μ.

NMR ($CDCl_3$) δ1.68 (s), 6H; 3.6 (s), 3H.

EXAMPLE VI

Preparation of N-Methyl-N-(2-Cyano-2-propanesulfenyl) carbamoyl fluoride

Anhydrous hydrogen chloride was bubbled through a stirred mixture of 37.65 g of N-methyl-N-chlorosulfenyl carbamoyl fluoride and 19.82 g of isobutyronitrile for 30 min. at room temperature. After stirring for 72 hr. the reaction mixture was distilled to yield 41.4 g of yellow oil b.p. 50° C./5 mm. $N_D^{24}$ 1.5011.

Infra-red (neat) 4.41 (C≡N), 5.52 (C═O), 6.4, 6.8, 7.6, 8.1, 9.1, 9.25, 10.35 and 13.25μ.

NMR ($CDCl_3$) δ1.65 (s), 6H; 3.51 (d), J=1.0 $H_Z$, 3H.

Calc'd. for $C_6H_9FN_2OS$: C, 40.89; H, 5.15; N, 15.90 Found: C, 40.19; H, 5.06; N, 15.47.

EXAMPLE VII

Preparation of N-Methyl-N-(2-cyano-2-propanethiosulfenyl) carbamoyl fluoride

To a mixture of 36.66 g of anhydrous hydrogen fluoride in 300 ml of toluene cooled to −50° C. was added dropwise and with stirring, 104.3 ml of methyl isocyanate over a period of 40 min. After stirring for 1 hr. at 0° C., 306.94 g of 2-cyano-2-chlorothiosulfenylpropane dissolved in 500 ml of toluene was added followed by a slow addition of 185.0 g of triethylamine, whilst maintaining the temperature between 3° and 10° C. After stirring for a period of 3 hours, the reaction was quenched with water and the toluene solution was dried over magnesium sulfate. Removal of the solvent yielded 206.9 g of an oil which solidified on standing. Crystallization from hexaneisopropylether gave a solid with m.p. 42°-45° C.

Calc'd for $C_6H_9FN_2OS_2$: C, 34.60; H, 4.35; N, 13.45. Found: C, 34.55; H, 4.20; N, 13.33.

EXAMPLE VIII

Preparation of 2-[[O-[N-Methyl-N-(2-chloromethyl-2-propanesulfenyl)carbamoyl]oximino]]-1,4-dithiane To a solution of 1.4 g of N-methyl-N-(2-chloromethyl-2-propanesulfenyl)carbamoyl chloride and 0.966 g of 2-oximino-1,4-dithiane in 50 ml of dioxane, was added dropwise with stirring 0.76 g of triethylamine. After allowing the reaction mixture to stand at ambient temperature for 16 hours it was diluted with water and extracted into ethylacetate. The organic extract was washed with water, dried over sodium sulfate and concentrated under reduced pressure. The product was crystallized from isopropyl ether-methylene chloride solution. The weight of first crop was 1.0 g. m.p. 116°-117° C.

Calc'd for $C_{10}H_{17}ClN_2O_2S_3$: C, 36.51; H, 5.21; N, 8.52 Found: C, 36.45; H, 5.01; N, 8.42.

EXAMPLE IX

Preparation of 3,5,5-Trimethyl-2-[[-O-[N-methyl-N-(2-methyl-1,3-dichloro-2-propanesulfenyl)carbamoyl] oximino]]-4-thiazolidinone To a solution of 3.28 g of 3,5,5-trimethyl-2-oximino-4-thiazolidinone and 5.0 g of N-methyl-N-(2-methyl-1,3-dichloro-2-propanesulfenyl)carbamoyl fluoride in 75 ml of dioxane, was added dropwise with stirring 2.18 g of triethylamine. The spontaneous exotherm raised the temperature to 30° C. After following the reaction mixture to stand at room temperature for 16 hours, the reaction mixture was diluted with 300 ml of water. The product was isolated in ethylacetate and purified by column chromatography over silica gel to yield 3.0 g of a white solid. m.p. 91°-92° C.

Calc'd for $C_{12}H_{19}Cl_2N_3O_3S_2$: C, 37.11; H, 4.93; N, 10.82 Found: C, 37.10; H, 4.99; N, 10.78.

EXAMPLE X

Preparation of 1-Methylthioacetaldehyde O-[N-methyl-N-(2-cyano-2-propanesulfenyl)carbamoyl]oxime To a stirred suspension of 4.12 g of 1-methylthioacetaldoxime and 7.05 g of N-methyl-N-(2-cyano-2-propanesulfenyl)carbamoyl fluoride in 50 ml of toluene was added 3.96 g of triethylamine diluted in 25 ml of toluene. The reaction mixture was left stirring at ambient temperature for 19 hours. It was diluted with an additional 50 ml of toluene and was washed with water. The organic extract was dried over magnesium sulfate and concentrated under reduced pressure to an oily residue. The product crystallized from isopropyletherethylacetate to yield 5.5 g of a white solid. m.p. 77°-78° C.

Calc'd for $C_9H_{15}N_3O_2S_2$: C, 41.36; H, 5.78; N, 16.08. Found: C, 41.33; H, 5.68; N, 15.98.

EXAMPLE XI

Preparation of 2-Methylthio-2-methylpropionaldehyde O-[N-methyl-N-(2-chloromethyl-2-propanesulfenyl)-carbamoyl] oxime Prepared as in Example I by reacting 2-methylthio-2-methylpropionaldoxime with N-methyl-N-(2-chloromethyl-2-propanesulfenyl)carbamoyl chloride in the presence of triethylamine as an acid acceptor. The product was isolated as an oil.

Infra-red (neat) 5.8μ (C=O), 6.2 (C≡N), 10.45 (N-O)μ among other bands.

NMR ($CDCl_3$) δ1.36 (S), 6H; 1.48 (S), 6H; 1.99 (S), 3H; 3.35 (S), 3H; 3.73 (S), 2H; 7.50 (S) 1H.

EXAMPLE XII

Preparation of 1-Methylthioacetaldehyde O-[N-methyl-N-(2-chloromethyl-2-propanesulfenyl)-carbamoyl]oxime Prepared as in Example I by reacting 1-methylthioacetaldoxime and N-methyl-N-(2-chloromethyl-2-propanesulfenyl)carbamoyl chloride in the presence of triethylamine. The product was isolated as a white solid, m.p. 55°-56° C.

Calc'd for $C_9H_{17}ClN_2O_2S_2$: C, 37.95; H, 6.02; N, 9.84. Found: C, 37.71; H, 6.13; N, 9.75.

Examples XIII to XXXV were prepared by using the methods of Examples VIII to XII. Their physical properties are listed in Table I below.

TABLE I

| | | | ELEMENTAL ANALYSIS | | | | | |
|---|---|---|---|---|---|---|---|---|
| | | | CALCULATED | | | FOUND | | |
| EXAMPLE | COMPOUND | M.P. °C. | C | H | N | C | H | N |
| XIII | 3,5,5-Trimethyl-2-[[O—[N—methyl-N—(2-chloromethyl-2-propanesulfenyl)carbamoyl]oximino]]-4-thiazolidinone | 83-85 | 40.72 | 5.70 | 11.87 | 39.90 | 5.80 | 11.52 |
| XIV | 5-Methyl-4-[[O—[N—methyl-N—(2-chloromethyl-2-propanesulfenyl) carbamoyl]oximino]]-1,3-oxathiolane | Oil | 38.39 | 5.48 | 8.96 | 38.58 | 5.56 | 9.16 |
| XV | 2-[[O—[N—methyl-N—(1,3-dichloro-2-methyl-2-propanesulfenyl)carbamoyl] oximino]]-1,4-dithiane | 104-105 | 33.05 | 4.44 | 7.71 | 32.78 | 4.30 | 7.76 |
| XVI | 2-Methylthio-2-methylpropionaldehyde O—[N—methyl-N—(1,3-dichloro-2-methyl-2-propanesulfenyl)carbamoyl] oxime | 71-72 | 38.04 | 5.80 | 8.07 | 37.99 | 5.91 | 8.07 |
| XVII | 1-Isopropylthioacetaldehyde O—[N—methyl-N—(1,3-dichloro-2-methyl-2-propanesulfenyl)carbamoyl]oxime | 57-58 | 38.03 | 5.80 | 8.07 | 37.68 | 5.56 | 7.91 |
| XVIII | 1-Methylthioacetaldehyde O—[N—methyl-N—(1,3-dichloro-2-methyl-2-propanesulfenyl)carbamoyl]oxime | Oil | 33.85 | 5.05 | 8.78 | 34.41 | 5.13 | 34 |
| XIX | 3,5,5-Trimethyl-2-[[O—[N—methyl-N—(1-chloro-2-cyano-2-propanesulfenyl)carbamoyl]oximino]]-4-thiazolidinone | 111-113 | 39.50 | 4.70 | 15.36 | 39.34 | 4.65 | 15.18 |
| XX | 2-[[O—[N—methyl-N—(1-chloro-2-cyano-2-propanesulfenyl)carbamoyl] oximino]]-1,4-dithiane | 93-95 | 35.34 | 4.15 | 12.36 | 35.86 | 4.05 | 12.24 |
| XXI | 2-Methylthio-2-methylpropionaldehyde O—[N—methyl-N—(1-chloro-2- | 53-55 | 40.79 | 5.60 | 12.97 | 41.23 | 5.65 | 12.77 |

TABLE I-continued

| EXAMPLE | COMPOUND | M.P. °C. | ELEMENTAL ANALYSIS CALCULATED C | H | N | FOUND C | H | N |
|---|---|---|---|---|---|---|---|---|
| | cyano-2-propanesulfenyl)carbamoyl] oxime | | | | | | | |
| XXII | 2-Nitro-2-methylpropionaldehyde O—[N—(1-chloro-2-cyano-2-propanesulfenyl)carbamoyl]oxime | Oil | 37.21 | 4.68 | 17.36 | 38.03 | 4.54 | 16.75 |
| XXIII | 1-Isopropylthioacetaldehyde O—[N—methyl-N—(2-cyano-2-propanesulfenyl)carbamoyl]oxime | 88–89 | 45.65 | 6.62 | 14.52 | 45.65 | 6.60 | 14.47 |
| XXIV | 1-(2-Cyanoethylthio)acetaldehyde O—[N—methyl-N—(2-cyano-2-propanesulfenyl)carbamoyl]oxime | 77–78 | 43.98 | 5.37 | 18.65 | 43.91 | 5.34 | 18.43 |
| XXV | 5-Methyl-4-[[O—[N—methyl-N—(2-cyano-2-propanesulfenyl)carbamoyl] oximino]]-1,3-oxathiolane | 83–87 | 41.50 | 5.23 | 14.52 | 41.52 | 5.08 | 14.40 |
| XXVI | 2-[[O—[N—methyl-N—(2-cyano-2-propanesulfenyl)carbamoyl]oximino]]-1,4-dithiane | 139–141 | 39.32 | 4.95 | 13.76 | 39.13 | 4.99 | 13.55 |
| XXVII | 1-Methylthioacetaldehyde O—[N—methyl-N—2-cyano-2-propanethiosulfenyl)carbamoyl]oxime | 57.5–59 | 36.84 | 5.15 | 14.32 | 36.82 | 4.97 | 14.20 |
| XXVIII | 1-(2-Cyanoethylthio)acetaldehyde O—[N—methyl-N—(2-cyano-2-propanethiosulfenyl)carbamoyl]oxime | 76–77 | 39.74 | 4.85 | 16.85 | 39.80 | 4.78 | 16.88 |
| XXIX | 1-Isopropylthioacetaldehyde O—[N—methyl-N—(2-cyano-2-propanethiosulfenyl)carbamoyl]oxime | 47–48 | 41.22 | 5.66 | 13.11 | 41.24 | 6.14 | 13.09 |
| XXX | 2-Methyl-2-propenal O—[N—methyl-N—(2-cyano-2-propanethiosulfenyl) carbamoyl]oxime | 69–70.5 | 43.93 | 5.53 | 15.37 | 43.53 | 5.37 | 15.34 |
| XXXI | 2-Nitro-2-methylpropionaldehyde O—[N—methyl-N—(2-cyano-2-propanethiosulfenyl)carbamoyl]oxime | 88–89 | 37.48 | 5.03 | 17.49 | 37.39 | 4.94 | 17.23 |
| XXXII | 2-Cyano-2-methylpropionaldehyde O—[N—methyl-N—(2-cyano-2-propanethiosulfenyl)carbamoyl]oxime | 123–124 | 43.98 | 5.37 | 18.65 | 43.85 | 5.35 | 18.64 |
| XXXIII | 2-Methylthio-2-methylpropionaldehyde O—[N—methyl-N—(2-cyano-2-propanethiosulfenyl)carbamoyl] oxime | 51.5–52.5 | 41.09 | 5.96 | 13.07 | 41.10 | 5.90 | 13.07 |
| XXXIV | 5-Methyl-4-[[O—[N—methyl-N—(2-cyano-2-propanethiosulfenyl) carbamoyl]oximino]]-1,3-oxathiolane | 58–60 | 37.36 | 4.70 | 13.07 | 37.28 | 4.64 | 13.06 |
| XXXV | 2-[[O—[N—methyl-N—(2-cyano-2-propanethiosulfenyl)carbamoyl] oximino]]-1,4-dithiane | 64–66 | 35.58 | 4.48 | 12.45 | 35.51 | 4.26 | 12.47 |

The following compounds are representative of other compounds that are within the scope of this invention which can be prepared according to the invention by selecting appropriate starting materials for use in the procedures described above:

1-(N',N'-Dimethylaminocarbonyl)-1-methylthioformaldehyde O-[N-methyl-N-(1,3-dichloro-2-methyl-2-propanesulfenyl) carbamoyl]oxime.

1-(N',N'-Dimethylaminocarbonyl)-1-methylthioformaldehyde O-[N-methyl-N-(2-cyano-2-propanethiosulfenyl)carbamoyl] oxime.

2-[[O-[N-Methyl-N-(1-chloro-2-cyano-2-propanesulfenyl) carbamoyl]oximino]]-1,3-dithiolane.

2-[[O-[N-Methyl-N-(1,3-dichloro-2-methyl-2-propanesulfenyl) carbamoyl]oximino]]-1,3-dithiolane.

1-Methylthio-3,3-dimethylbutanone-2 O-[N-methyl-N-(1,3-dichloro-2-methyl-2-propanesulfenyl)carbamoyl]oxime.

1-Methylthio-3,3-dimethylbutanone-2 O-[N-methyl-N-(2-cyano-2-methyl-2-propanethiosulfenyl)carbamoyl-]oxime.

1-Methylthio-3,3-dimethylbutanone-2 O-[N-methyl-N-(2-cyano-2-methyl-2-propanethiosulfenyl)carbamoyl-]oxime.

1-(2-Cyanoethylthio)acetaldehyde O-[N-methyl-N-(1,3-dichloro-2-methyl-2-propanesulfenyl)carbamoyl]oxime.

2-[[O-[N-Methyl-N-(2-cyano-2-propanesulfenyl)carbamoyl] oximino]]-4,5,5-trimethylthiazolidin-3-one.

2-[[O-[N-Methyl-N-(1,3-dichloro-2-methyl-2-propanesulfenyl) carbamoyl]oximino]]-4,5,5-trimethylthiazolidin-3-one.

2-[[O-[N-Methyl-N-(2-cyano-2-propanethiosulfenyl)-carbamoyl] oximino]]-4,5,5-trimethylthiazolidin-3-one.

1-methylthiopyruvaldehyde O-[N-methyl-N-(1-chloro-2-cyano-2-propanesulfenyl)carbamoyl]oxime.

1-Methylthiopyruvaldehyde O-[N-methyl-N-(2-cyano-2-propanethiosulfenyl)carbamoyl]oxime.

1-Ethylthiopyruvaldehyde O-[N-methyl-N-(2-cyano-2-propanesulfenyl)carbamoyl]oxime.

1-Ethoxycarbonyl-1-methylthioformaldehyde O-[N-methyl-N-(1,3-dichloro-2-methyl-2-propanesulfenyl)-carbamoyl] oxime.

1-Ethoxycarbonyl-1-methylthioformaldehyde O-[N-methyl-N-(2-cyano-2-propanesulfenyl)carbamoyl]oxime.

1-Ethoxycarbonyl-1-methylthioformaldehyde O-[N-methyl-N-(2-cyano-2-propanethiosulfenyl)carbamoyl]oxime.

2-[[O-[N-Methyl-N-(2-cyano-2-propanethiosulfenyl) carbamoyl]oximino]]-4-methyltetrahydro-1,4-thiazin-3-one.

2-[[O-[N-Methyl-N-(1,3-dichloro-2-methyl-2-propanesulfenyl) carbamoyl]oximino]]-4-methyltetrahydro-1,4-thiazin-3-one.

2-[[O-[N-Methyl-N-(2-cyano-2-propanesulfenyl)carbamoyl] oximino]]-3-isopropylthiazolidin-4-one.

2-[[O-[N-Methyl-N-(2-cyano-2-propanethiosulfenyl)-carbamoyl] oximino]]-3,5,5-trimethylthiazolidin-4-one.

4-[[O-[N-Methyl-N-(1,3-dichloro-2-methyl-2-propanesulfenyl) carbamoyl]oximino]]-5,5-dimethyl-1,3-dithiolane.

4-[[O-[N-Methyl-N-(2-cyano-2-propanethiosulfenyl)-carbamoyl] oximino]]-5-methyl-1,3-dithiolane.

2-[[O-[N-Methyl-N-(1,3-dichloro-2-methyl-2-propanesulfenyl) carbamoyl]oximino]]-1,3,5-trithiane.

2-[[O-[N-Methyl-N-(2-cyano-2-propanesulfenyl)carbamoyl] oximino]]-1,3,5-trithiane.

4-[[O-[N-Methyl-N-(2-cyano-2-propanethiosulfenyl)-carbamoyl] oximino]]-1,3,5-oxadithiane.

2-[[O-[N-Methyl-N-(2-cyano-2-propanethiosulfenyl)-carbamoyl] oximino]]-1,3,5-trithiane-5,5-dioxide.

2-[[O-[N-Methyl-N-(2-cyano-2-propanethiosulfenyl)-carbamoyl] oximino]]-thiophane.

2-[[O-[N-Methyl-N-(1,3-dichloro-2-methyl-2-propanesulfenyl) carbamoyl]oximino]]-4-vinyl-1,3-dithiolane.

3-[[O-[N-Methyl-N-(2-cyano-2-propanethiosulfenyl)-carbamoyl] oximino]]-2,2-dimethylthiophane.

2-Methylsulfonyl-2-methylpropionaldehyde O-[N-Methyl-N-(1,3-dichloro-2-propanesulfenyl)carbamoyl]oxime.

2-Methylsulfonyl-2-methylpropionaldehyde O-[N-methyl-N-(2-cyano-2-propanethiosulfenyl)carbamoyl]oxime.

α-Cyanobenzaldehyde O-[N-methyl-N-(2-cyano-2-propanethiosulfenyl)carbamoyl]oxime.

1,2-Dicyano-2-methylpropionaldehyde O-[N-methyl-N-(2-cyano-2-propanethiosulfenyl)carbamoyl]oxime.

2-[[O-[N-Methyl-N-(1,3-dichloro-2-methyl-2-propanesulfenyl) carbamoyl]oximino]]-1,3-oxathiolane.

2-[[O-[N-Methyl-N-(2-cyano-2-propanethiosulfenyl)-carbamoyl] oximino]]-1,4-dioxane.

2-[[O-[N-Methyl-N-(1,3-dichloro-2-methyl-2-propanesulfenyl) carbamoyl]-oximino]]1,4-dioxane.

2-[[O-[N-Methyl-N-(1,3-dichloro-2-methyl-2-propanesulfenyl) carbamoyl]oximino]]-4-methyltetrahydro-1,4-thiazin-5-one.

2-[[O-[N-Methyl-N-(1-chloro-2-cyano-2-propanesulfenyl) carbamoyl]oximino]]-4-methyltetrahydro-1,4-thiazin-5-one.

3[[O-[N-Methyl-N-(1,3-dichloro-2-methyl-2-propanesulfenyl) carbamoyl]oximino]]-1,4-oxathiane.

2-[[O-[N-Methyl-N-(2-cyano-2-propanethiosulfenyl)-carbamoyl] oximino]]-4-methyl-tetrahydro-1,4-oxazin-3-one.

2-[[O-[N-Methyl-N-(1-chloro-2-cyano-2-propanesulfenyl) carbamoyl]oximino]]-1,4-dithiane-4-oxide.

2-(3-Methyl-2-dithiolanyl)propionaldehyde O-[N-methyl-N-(1,3-dichloro-2-methyl-2-propanesulfenyl)carbamoyl]oxime.

2-[[O-[N-Hexyl-N-(2-cyano-2-bicyclo[2.2.1]heptanethiosulfenyl)carbamoyl]oximino]]-4-methyl tetrahydro-1,4-thiazin-5-one.

2-[[O-[N-Octyl-N-(2-chloro-1-cyclohexanesulfenyl) carbamoyl]oximino]]-1,4-dithiane-4-oxide.

4-[[O-[N-Propyl-N-(2-chloro-1-methyl-1-cyclopentanethiosulfenyl)carbamoyl]oximino]]-5,5-dimethyl-1,3-dithiolane.

Selected species of the new compounds were evaluated to determine their pesticidal activity against nematodes, mites and certain insects, including an aphid, a boll weevil, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the beam aphid (*Aphis fabae* Scop.) reared on potted dwarf nasturtium plants at 65°-70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infected plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulator by prodding were considered dead. Percent mortality was recorded for various concentration levels.

Southern Armyworm Leaf Spray Test

Larvae of the southern armyworm (*Prodenia Eridania*, (Cram.), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig. air pressure.

This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis,* Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica,* L.) reared according to the specifications of the Chemical Specialties Manufacturing Association (Blue Book, McNair-Dorland Co., NY., 1954; pages 243–244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard foot strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

Mite Foliage Spray Test

Adults and nymphal stages of the two-spotted mite (*Tetranychus urticae Koch*), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted for 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding, was considered living.

Nematocide Test

The test organism used was the infective migratory larvae of the root-knot nematode, *Meloidogyne incognita var. acrita,* reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests are set forth in Table I below. In these tests the pesticidal activity of the compounds against aphid, mite, Southern Armyworm, Mexican Bean Beetle, nematode and house fly was rated as follows:

A=Excellent control
B=Partial control
C=No control

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these rats are set forth in Table I below:

TABLE II (Biological Data)

| Example No. | Compound | Aphid | Mite | Southern Army-worm | Mexican Bean Beetle | House-fly | Nema-tode | A.O. Rat. mg/kg |
|---|---|---|---|---|---|---|---|---|
| VIII | 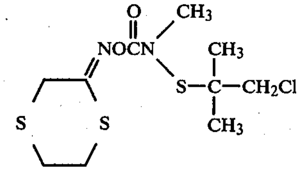 | A | A | A | A | A | A | 24. |
| IX | 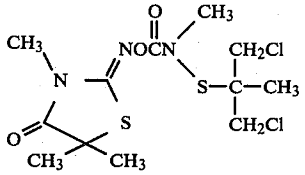 | B | C | A | A | A | C | 343 |
| X | 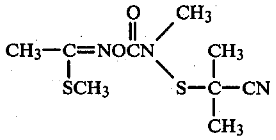 | A | A | A | A | A | — | 127 |
| XI | 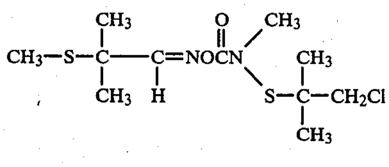 | A | A | C | A | A | B | — |
| XII | 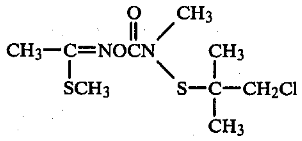 | A | C | A | A | A | A | 104 |
| XIII | 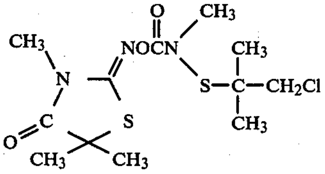 | A | C | A | A | A | B | 343 |
| XIV | 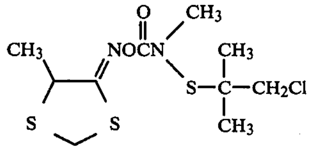 | A | A | A | A | A | C | — |
| XV | 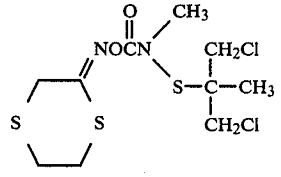 | A | A | A | A | A | A | 43 |

TABLE II-continued
(Biological Data)
| Example No. | Compound | Aphid | Mite | Southern Army-worm | Mexican Bean Beetle | House-fly | Nema-tode | A.O. Rat. mg/kg |
|---|---|---|---|---|---|---|---|---|
| XVI | 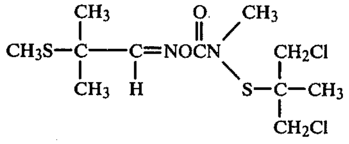 | A | A | A | A | A | C | 2.5 |
| XVII | 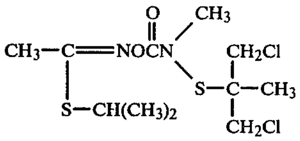 | A | A | A | A | A | — | 174 |
| XVIII | 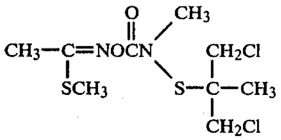 | A | A | A | A | A | — | — |
| XIX | 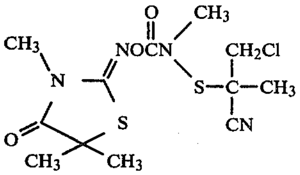 | A | C | A | A | A | C | 320 |
| XX | 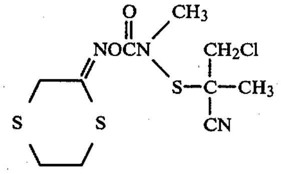 | A | A | A | A | A | A | 40 |
| XXI | 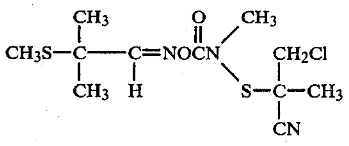 | A | A | A | A | A | A | — |
| XXII | 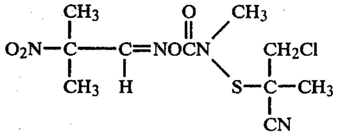 | A | A | A | A | A | A | — |
| XXIII | 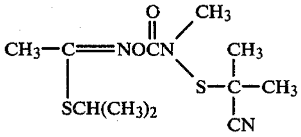 | A | A | A | A | A | C | 20 |
| XXIV | 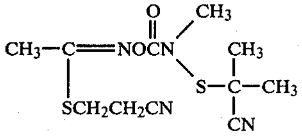 | A | A | A | A | A | C | 14.1 |
| XXV | 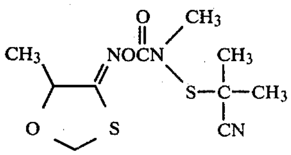 | A | A | A | A | A | B | — |

TABLE II-continued

| Example No. | Compound | Aphid | Mite | Southern Army-worm | Mexican Bean Beetle | House-fly | Nema-tode | A.O. Rat. mg/kg |
|---|---|---|---|---|---|---|---|---|
| | | (Biological Data) | | | | | | |
| XXVI | 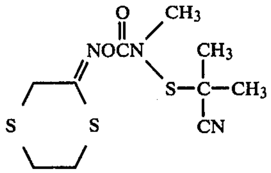 | A | A | A | A | A | B | 40 |
| XXVII | 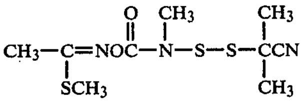 | A | A | A | A | A | — | 127 |
| XXVIII | 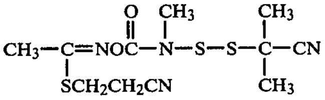 | A | A | A | A | A | — | 28 |
| XXIX | 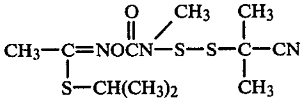 | A | A | A | A | A | — | 18 |
| XXX | 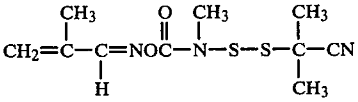 | A | C | B | A | A | — | — |
| XXXI | 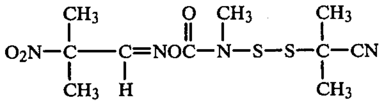 | A | A | A | A | A | — | — |
| XXXII | 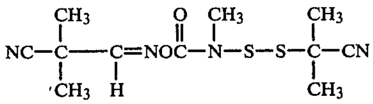 | B | A | A | A | A | — | 14 |
| XXXIII | 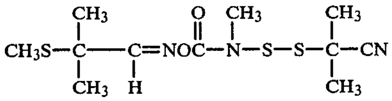 | A | A | B | A | A | — | — |
| XXXIV | 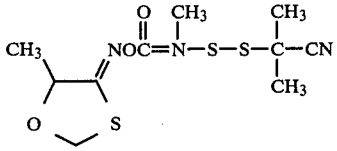 | A | A | A | A | A | — | 14 |
| XXXV | 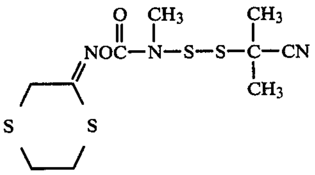 | A | A | A | A | A | — | 32 |

The data in TABLE II clearly illustrates the broad spectrum high level pesticidal activity exhibited by the compounds of this invention. It should be understood that the pests evaluated are representative of a wider variety of pest which can be controlled by the compounds of this invention.

To more clearly illustrate the novelty and the outstanding biological properties of the compounds of this invention, comparison tests were conducted utilizing the test procedures described above. More specifically, comparison tests were conducted to evaluate the relative pesticidal activity and mammalian toxicity of certain representative compounds of this invention and their parent carbamate compounds.

Pesticidal test results are expressed in $LD_{50}$'s, the parts of test compound per million parts of final formulation required to achieve a 50% mortality of the subject pest and the mammalian toxicity test results are expressed in milligrams of compound per kilogram of body weight of the animal required to achieve a 50% mortality rate. The subject mammal was in all cases a rat.

The test results of the comparison tests are set forth in TABLE III below.

TABLE III

COMPARISON TEST RESULTS

| No. | Compound | Aphid | Mite | Southern Armyworm | Mexican Bean Beetle | Housefly | A.O. Rat. $LD_{50}$ mg/kg |
|---|---|---|---|---|---|---|---|
| | | BIOLOGICAL DATA | | | | | |
| 1 | 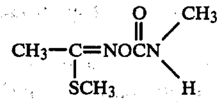 known parent compound | 3 | 500 | 9 | 30 | 5 | 49 |
| 2 | 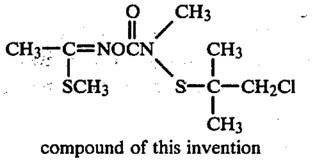 compound of this invention | 2 | 500 | 15 | 30 | 8 | 104 |
| 3 | 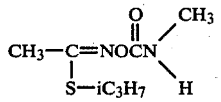 known parent compound | 9 | 350 | 27 | 62 | 8 | 8 |
| 4 | 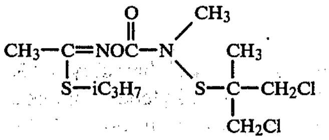 Compound of this invention. | 13 | 35 | 30 | 15 | 17 | 174 |

The results set forth in TABLE III clearly indicate that the pesticidal activity of the compounds of this invention is equivalent or superior to that of the corresponding parent compounds. More significant is the dramatic reduction in mammalian toxicity of the compounds of this invention in comparison to the corresponding parent carbamate compounds in all compounds evaluated. For example, parent carbamate compound 1 is two times more toxic to mammals than compound 2, the corresponding carbamate compound of this invention. Parent carbamate compound 3 is twenty-one times more toxic to mammals than compound 4, the corresponding carbamate compound of this invention.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about $\frac{1}{4}$ to 15 pound of active toxicant per acre.

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characeristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. An insecticidal, miticidal or nematocidal composition comprising an acceptable carrier and as active toxicant an insecticidally, miticidally or nematocidally effective amount of a compound of the formula:

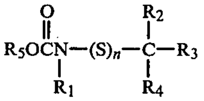

wherein:

n is 1 or 2;

$R_1$ is alkyl;

$R_2$ and $R_3$ are individually alkyl, haloalkyl or $R_2$ and $R_3$ together may form an alkylene chain completing either a substituted or an unsubstituted cyclopentyl, cyclohexyl or a 6, 7 or 8 membered bicycloalkyl ring wherein the permissible substituents are one or more fluoro, chloro, bromo, alkyl or haloalkyl substituents in any combination;

$R_4$ is hydrogen, alkyl, chloro or cyano with the proviso that when $R_2$ and $R_3$ are both alkyl, $R_4$ may not be hydrogen or alkyl;

$R_5$ is

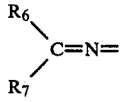

$R_6$ is hydrogen, chloro, alkyl, alkylthio or cyanoalkylthio; and $R_7$ is chloro, carbamoyl, alkylcarbamoyl, amido dialkylcarbamoyl, dithiolanylalkyl or either substituted or unsubstituted alkyl, alkenyl, alkylthio, alkoxyalkyl, alkanoyl, phenyl or alkoxycarbonyl wherein the permissible substituents are one or more fluoro, chloro, bromo, cyano, nitro, alkylthio, alkylsulfinyl, alkylsulfonyl, alkoxy, carbamoyl, alkylcarbamoyl or dialkylcarbamoyl substituents; with the proviso that $R_1$, $R_2$, $R_3$, $R_4$, $R_6$ and $R_7$ substituents individually may not include more than eight aliphatic carbon atoms.

2. A composition according to claim 1 wherein $R_1$ is alkyl having from 1 to 4 carbons.

3. A composition according to claim 1 wherein $R_1$ is methyl.

4. A composition according to claim 1 wherein $R_2$ and $R_3$ are individually alkyl or chloroalkyl.

5. A composition according to claim 1 wherein $R_2$ and $R_3$ are individually methyl or chloromethyl.

6. A composition according to claim 1 wherein $R_4$ is cyano or chloroalkyl.

7. A composition according to claim 1 wherein $R_4$ is chloromethyl.

8. A composition according to claim 1 wherein $R_6$ is hydrogen, alkyl, alkylthio or cyanoalkylthio.

9. A composition according to claim 1 wherein $R_7$ is alkyl, alkylthio, alkoxycarbonyl, carbamoyl, alkylcarbamoyl, dialkylcarbamoyl, alkylthioalkyl, alkylsulfinylalkyl, alkylsulfonylalkyl, cyanoalkyl, nitroalkyl, cyanoalkylthio or amido.

10. A composition according to claim 1 wherein the active toxicant is 1-Methylthioacetaldehyde O-[N-methyl-N-(2-chloromethyl-2-propanesulfenyl)carbamoyl]oxime.

11. A composition according to claim 1 wherein the active toxicant is 1-Isopropylthioacetaldehyde O-[N-methyl-N-(1,3-dichloro-2-methyl-2-propanesulfenyl)-carbamoyl] oxime.

12. A composition according to claim 1 wherein the active toxicant is 1-Methylthioacetaldehyde O-[N-methyl-N-(2-cyano-2-propanethiosulfenyl)carbamoyl-]oxime.

13. A method of controlling insects, mites and nematodes which comprises subjecting them to an insecticidally, miticidally or nematocidally effective amount of a compound of the formula:

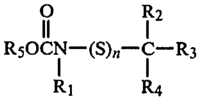

wherein:

n is 1 or 2;

$R_1$ is alkyl;

$R_2$ and $R_3$ are individually alkyl, haloalkyl or $R_2$ and $R_3$ together may form an alkylene chain completing either a substituted or an unsubstituted cyclopentyl, cyclohexyl or a 6, 7 or 8 membered bicycloalkyl ring wherein the permissible substituents are one or more fluoro, chloro, bromo, alkyl or haloalkyl substituents in any combination;

$R_4$ is hydrogen, alkyl, chloro or cyano with the proviso that when $R_2$ and $R_3$ are both alkyl, $R_4$ may not be hydrogen or alkyl;

$R_5$ is

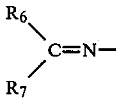

$R_6$ is hydrogen, chloro, alkyl, alkylthio or cyanoalkylthio; and $R_7$ is chloro, carbamoyl, alkylcarbamoyl, amido dialkylcarbamoyl, dithiolanylalkyl or either substituted or unsubstituted alkyl, alkenyl, alkylthio, alkoxyalkyl, alkanoyl, phenyl or alkoxycarbonyl wherein the permissible substituents are one or more fluoro, chloro, bromo, cyano, nitro, alkylthio, alkylsulfinyl, alkylsulfonyl, alkoxy, carbamoyl, alkylcarbamoyl or dialkylcarbamoyl substituents; with the proviso that $R_1$, $R_2$, $R_3$, $R_4$, $R_6$ and $R_7$ substituents individually may not include more than eight aliphatic carbon atoms.

14. A method according to claim 13 wherein $R_1$ is alkyl having from 1 to 4 carbons.

15. A method according to claim 13 wherein $R_1$ is methyl.

16. A method according to claim 13 wherein $R_2$ and $R_3$ are individually alkyl or chloroalkyl.

17. A method according to claim 13 wherein $R_2$ and $R_3$ are individually methyl or chloromethyl.

18. A method according to claim 13 wherein $R_4$ is cyano or chloroalkyl.

19. A method according to claim 13 wherein $R_4$ is chloromethyl.

20. A method according to claim 13 wherein $R_6$ is hydrogen, alkyl, alkylthio or cyanoalkylthio.

21. A method according to claim 13 wherein $R_7$ is alkyl, alkylthio, alkoxycarbonyl, carbamoyl, amido, alkylcarbamoyl, dialkylcarbamoyl, alkylthioalkyl, alkylsulfinylalkyl, alkylsulfonylalkyl, cyanoalkyl, nitroalkyl or cyanoalkylthio.

22. A method according to claim 13 wherein the compound is 1-Methylthioacetaldehyde O-[N-methyl-N-(2-chloromethyl-2-propanesulfenyl)carbamoyl]oxime.

23. A method according to claim 13 wherein the compound is 1-Isopropylthioacetaldehyde O-[N-methyl-N-(1,3-dichloro-2-methyl-2-propanesulfenyl)carbamoyl] oxime.

24. A method according to claim 13 wherein the compound is 1-Methylthioacetaldehyde O-[N-methyl-N-(2-O-[N-methyl-N-(2-cyano-2-propanethiosulfenyl) carbamoyl].

* * * * *

UNITED STATES PATENT AND TRADEMARK OFFICE

CERTIFICATE OF CORRECTION

PATENT NO. : 4,485,113

DATED : November 27, 1984

INVENTOR(S) : Themistocles D.J. D'Silva

It is certified that error appears in the above-identified patent and that said Letters Patent is hereby corrected as shown below:

In the claims, claim 24, lines 12-14, that portion reading "1-Methylthioacetaldehyde 0-[N-methyl-N-(2-0-[N-methyl-N-(2-cyano-2-propanethiosulfenyl)carbamoyl]" should read -- 1-Methylthioacetaldehyde 0-[N-methyl-N-(2-cyano-2-propanethiosulfenyl)carbamoyl] oxime --.

In the claims, claim 1, line 40, that portion reading

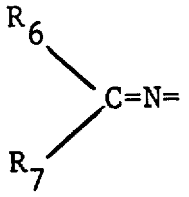

should read

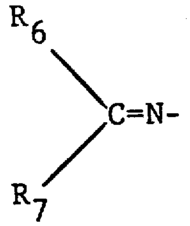

.

Signed and Sealed this

*Seventh* Day of *May 1985*

[SEAL]

*Attest:*

DONALD J. QUIGG

*Attesting Officer* *Acting Commissioner of Patents and Trademarks*